United States Patent [19]
Williams

[11] Patent Number: 5,332,107
[45] Date of Patent: Jul. 26, 1994

[54] DENTAL CARE CENTER

[75] Inventor: Kenneth A. Williams, Cape Town, South Africa

[73] Assignee: Camps Limited, Channel Islands, United Kingdom

[21] Appl. No.: 919,856

[22] Filed: Jul. 27, 1992

[30] Foreign Application Priority Data

Jul. 29, 1991 [ZA] South Africa ............. 91/5912
Oct. 4, 1991 [ZA] South Africa ............. 91/7966

[51] Int. Cl.⁵ ............................................. A47K 1/09
[52] U.S. Cl. ............................... 211/88; 206/362.3; 206/362.1; 132/309
[58] Field of Search ............. 211/87, 88, 89, 118; 206/361, 362, 362.1, 362.2, 362.3, 63.5, 581; 132/323–325, 308, 309, 310; D6/528, 534; 312/245

[56] References Cited

U.S. PATENT DOCUMENTS

| | | | |
|---|---|---|---|
| D. 162,978 | 4/1951 | Neumann | D6/534 |
| 1,506,257 | 8/1924 | Schmidt | 132/310 X |
| 1,527,832 | 2/1925 | Bragg et al. | 211/65 X |
| 2,655,968 | 3/1951 | Simmons . | |
| 2,712,487 | 7/1955 | Miller | 312/245 X |
| 3,138,414 | 6/1964 | LaPollo | 312/245 X |
| 3,228,737 | 1/1966 | Kipnis . | |
| 3,977,743 | 8/1976 | Harris . | |
| 4,008,808 | 2/1977 | Ramsey | 211/88 X |
| 4,944,440 | 7/1990 | Fortman . | |
| 5,016,661 | 5/1991 | Israel et al. | 132/324 |

FOREIGN PATENT DOCUMENTS 8910400 5/1990 Fed. Rep. of Germany .

Primary Examiner—P. Austin Bradley
Assistant Examiner—Jeanne M. Elpel

[57] ABSTRACT

The dental care structure disclosed includes a backing plate for mounting on a wall, a number of enclosures which are releasably secured to the backing plate, a supporting bar for a cup and a bifurcated support for a tube of toothpaste. The enclosures can be for the purpose of receiving and protecting the heads of toothbrushes or for receiving a reel of dental floss. Each enclosure includes a flap-type door and the door of the enclosure which receives the dental floss has a cutter mounted thereon. The cup has a groove in the base thereof which receives the supporting bar. The cup can hang inverted from the bar or can stand upright on it.

11 Claims, 2 Drawing Sheets

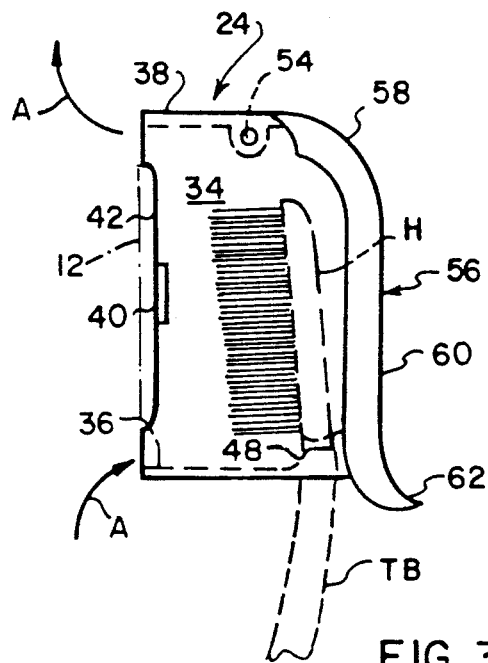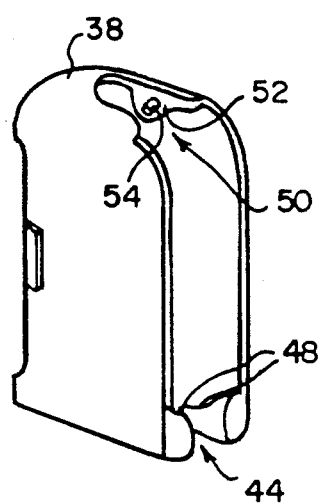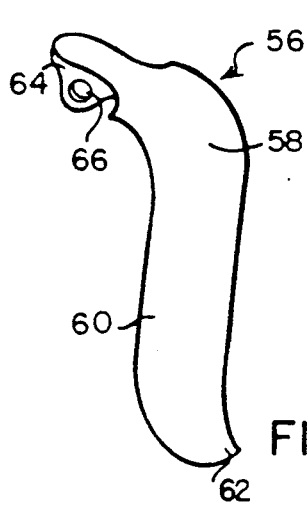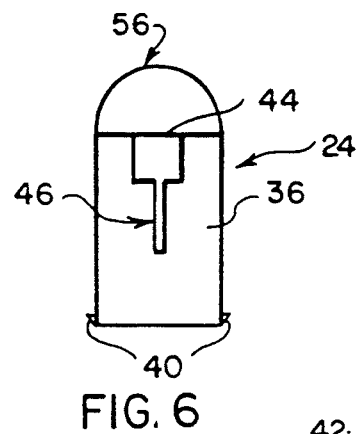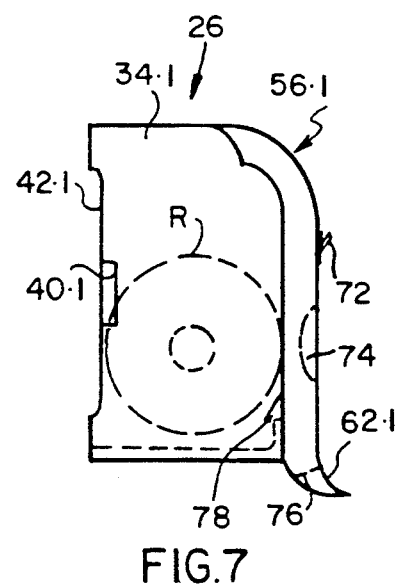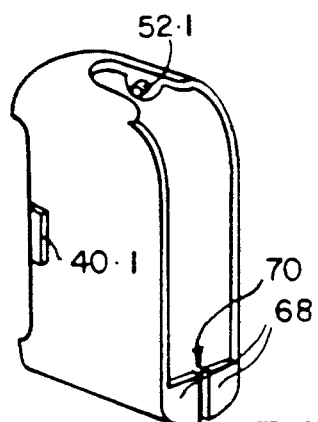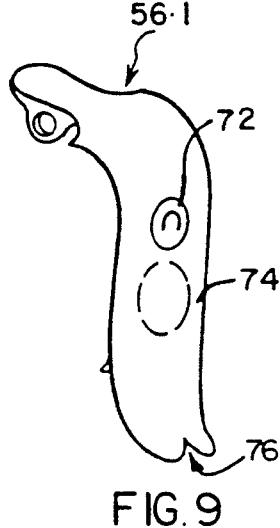

DENTAL CARE CENTER

This invention relates to a Dental Care Centre.

BACKGROUND TO INVENTION

A bathroom used by a family unit generally has in it toothbrushes, toothpaste, a cup or glass and dental floss. Quite often the toothbrushes and toothpaste will stand in the glass or cup or lie on a shelf and the dental floss will lie on a shelf or be retained in the manufacturer's original packaging. The toothbrush heads are uncovered and overall the dental care items are not in any way arranged in tidy or hygienic fashion.

OBJECT OF INVENTION

The present invention seeks to provide structures which enables dental care items to be stored hygienically and tidily arranged.

BRIEF SUMMARY OF INVENTION

According to one aspect of the present invention there is provided a toothbrush head enclosure comprising walling defining a space for receiving a toothbrush head, the walling bounding an entrance to said space and incorporating a cradle for supporting a toothbrush head which is within said space, the walling including a bottom wall which has a recess in an edge thereof through which recess the handle of a toothbrush, the head of which is supported by said cradle, can pass whereby the handle can hang down below said enclosure, and a door for closing off said entrance, the door having a first position in which it closes said entrance and a second position in which said entrance is open to enable a toothbrush head to be placed in said space for support by the cradle or removed from said space.

Said door can be in the form of a flap having its upper end pivotally mounted on said walling.

In the preferred form said enclosure comprises two side walls, the side walls having free vertically extending rear edges, and mounting means for the enclosure on the external faces of said side walls adjacent said rear edges.

Said bottom wall can include a water draining slot which forms an extension of said recess.

It is preferred that the cradle be constituted by protrusions extending upwardly from said bottom wall, and that said mounting means comprise protruding lugs on the external faces of said side walls adjacent said rear edges.

The present invention also provides the combination of an enclosure and a wall mounting plate including a recess into which said enclosure is inserted with said rear edges leading, vertical bounding faces of said recess including sockets for receiving said lugs of the enclosure thereby to mount the enclosure on said plate.

The combination can further include a support bar which protrudes from said plate and a cup having in the base thereof a slot in which said bar can be inserted to support said cup, the correct way up or inverted, on said bar, and can additionally comprise a toothpaste tube support protruding from said plate, said support being bifurcated so as to provide a recess into which a toothpaste tube can be pushed, the tube hanging vertically from said support.

According to a further aspect of the present invention there is provided a dental floss enclosure comprising walling defining a space for receiving a reel of dental floss, the walling bounding a front entrance to said space, a door in the form of a flap having its upper end pivotally mounted on said walling and having a notch in its lower edge through which dental floss can be run from the interior of said enclosure to the exterior, and a dental floss cutter on the outer face of said door.

According to another aspect of the present invention there is provided in combination a plate for mounting on a wall, the plate having at least one recess in the front face thereof, two opposed bounding faces of said recess having sockets therein, and an enclosure comprising walling defining a space, there being a front entrance to, the space within the enclosure and a door in the form of a flap which is pivotally mounted at its upper end on said walling, said door having a closed position in which it hangs down to close-off said entrance and being pivotable upwardly about its pivotal mounting to permit access to be had to said space, said space being open rearwardly and said walling including two outwardly protruding lugs which are received in said sockets when said enclosure is inserted into said recess whereby the interengaged sockets and lugs mount the enclosure on said plate.

BRIEF DESCRIPTION OF DRAWINGS

For a better understanding of the present invention, and to show how the same may be carried into effect, reference will now be made, by way of example, to the accompanying drawings in which:

FIG. 3 is a side elevation of an enclosure for the head of a toothbrush;

FIG. 4 is a pictorial view of the enclosure of FIG. 3 without its door;

FIG. 5 is a pictorial view of a door;

FIG. 6 is an underneath view of the enclosure of FIG. 3;

FIG. 7 is a side elevation of a dental floss enclosure;

FIG. 8 illustrates the enclosure of FIG. 7 without its door; and

FIG. 9 illustrates the door of the enclosure of FIG. 7.

DETAILED DESCRIPTION OF DRAWINGS

Figure 1:
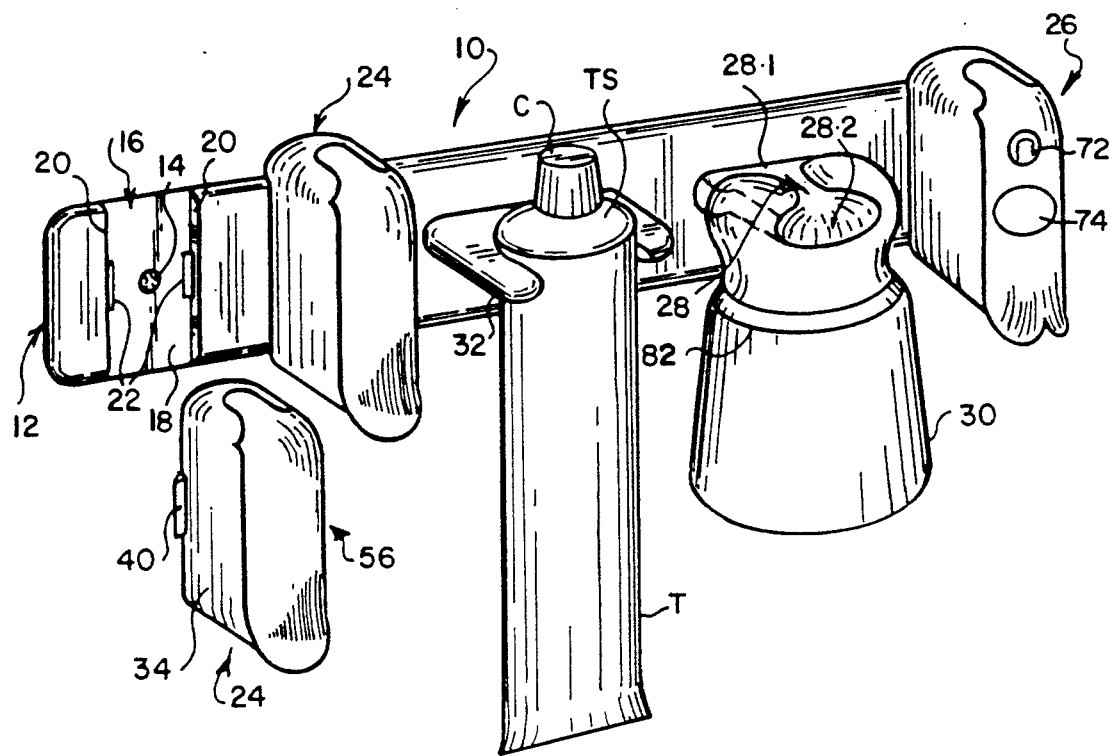
FIG. 1 is a pictorial view of a wall mounted structure which incorporates dental care items.

Referring firstly to FIG. 1, the structure illustrated is generally designated 10, and comprises a plate 12 which is horizontally elongate and which can be secured to a wall by screws passed through two screw holes 14, only one of which is visible in FIG. 1. The plate 12 can alternatively be mounted on a wall by means of double-sided adhesive tape.

A vertically extending recess 16 extends from the top edge of the plate 12 to the bottom edge and is bounded by a rear face 18 and two opposed side faces 20. Sockets 22 are provided in the bounding faces 20 of the recess 16.

Two toothbrush head enclosures 24 are shown in FIG. 1. The right hand enclosure 24 is shown attached to the plate 12 and the left hand enclosure 24 is shown detached from the plate 12. Behind the right hand enclosure 24 there is a second recess 16 which is completely concealed by the enclosure 24. A further enclosure 26 is mounted on the plate 12 and conceals a further recess 16.

A support bar 28 protrudes from the plate 12 and a cup 30 is hung from the bar 28. A bifurcated support 32 also protrudes horizontally from the plate 12 and this serves to support a tube of toothpaste which is designated T.

Figure 2:
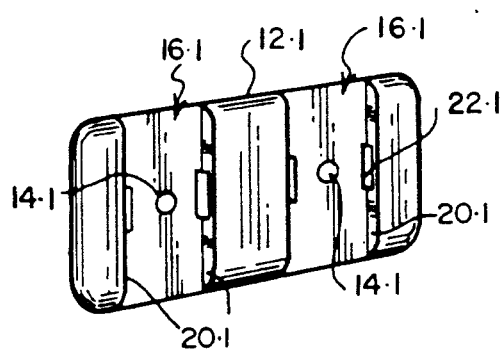
FIG. 2 illustrates a modification of the structure of FIG. 1.

In FIG. 2 there is illustrated a plate 12.1 which is formed with two recesses 16.1, the recesses 16.1 of FIG. 2 having the same configuration as the recesses 16 of FIG. 1. The plate 12.1 is secured to a wall (not shown) by screws passed through the holes 14.1. The bounding faces 20.1 of the recesses 16.1 have sockets 22.1 therein. The plate 12.1 can thus carry two enclosures 24 or one enclosure 24 and one enclosure 26.

Turning now to FIGS. 3 to 6, these illustrate an enclosure 24 in detail. The enclosure 24 illustrated comprises a "box" which is open both at the front and at the rear. The box is bounded by two vertical side walls 34, a bottom wall 36 and a top wall 38. Lugs 40 are provided on the external faces of the side walls 34 immediately adjacent the free rear edges 42 of the side walls 34. The lugs 40 are compatible in shape with the sockets 22.

The bottom wall 36 has a recess 44 (see particularly FIG. 6) in the front edge thereof, the recess 44 being extended rearwardly by a drainage slot 46. The recess 44 and slot 46 pass through the bottom wall 36. On each side of the recess 44 there is a protrusion 48. The two protrusions 48 form a cradle on which the head H (FIG. 3) of a toothbrush TB can be supported. As clearly shown in FIG. 3, the bristles of the toothbrush head H are held spaced from the bottom wall 36. The handle of the toothbrush is in the recess 44.

The top wall 38 has a slot 50 therein and on each side of the slot 50 there is a mount 52. Each mount 52 depends from the top wall 38 and includes a pin 54. The two pins 54 are co-axial with one another.

Reference numeral 56 (see particularly FIG. 5) designates a door which is in the form of a flap. The door includes an upper part 58 and a lower part 60, the parts 58 and 60 merging smoothly with one another and the lower end of the part 60 curving outwardly (see particularly FIG. 3) thereby to provide an operating element 62 for the door. Two brackets 64 depend from the upper part 58 of the door 56, each bracket 64 having a hole 66 therein. The door 56 is mounted on the enclosure 24 by squeezing the brackets 64 towards one another, inserting the upper part 58 of the door 56 into the slot 50 so that the pins 54 are aligned with the holes 66, and then releasing the brackets 64 so that they spring apart thereby interengaging the pins 54 with the holes 66 and pivotally mounting the door 56.

The side walls 34, top wall 38 and bottom wall 36 together constitute walling which defines a space for receiving a toothbrush head.

The enclosure 24 is mounted on the plate 12 by squeezing the side walls 34 towards one another. This reduces the distance between the lugs 40. The side walls 34 are then inserted into the recess 10. When the side walls 34 are subsequently released, the lugs 40 enter the sockets 22 and thereby releasably mount the enclosure 24 on the plate 12. As will be seen from FIG. 3, the edges 42 of the side walls 34 are rebated to receive the plate 12. The enclosure 24 extends both above and below the plate 12. It will be understood that, because the enclosure 24 does not have a back, there are inlets to the space within the enclosure 24 both above and below the plate 12. The arrows A in FIG. 3 indicate the way in which ventilating air can flow into and out of the enclosure through these inlets.

By squeezing the side walls 34 together, thereby to withdraw the lugs 40 from the sockets 22, the enclosure 24 can readily be removed from the plate 12 and washed out.

Turning now to FIGS. 7, 8 and 9, the enclosure 26 has many features in common with the enclosure 24. Where applicable, like parts have been designated with like reference numerals to which the suffix .1 has been added.

The protrusions 48, the recess 44 and the slot 46 are omitted from the enclosure 26 which consequently has an unapertured bottom wall. Two front wall portions 68 (FIG. 8) protrude upwardly from the bottom wall and there is a vertically extending slot 70 between the wall portions 68. On the outer face of the door 56.1 there is a double edged stainless steel floss cutter 72. Below the floss cutter 72 there is a depressed area 74.

The floss cutter 72 preferably comprises two tangs and a disc-like central portion between the tangs. The door 56.1 has an external depression for receiving said central portion and two apertures for receiving the tangs. The tangs are pushed through the apertures and the portions thereof which project from the inside of the door are bent over to secure the cutter in place.

If desired one or more additional cups and one or more additional plates each having a support 28 protruding therefrom can be provided.

The operating element 62.1 of the door 56.1 has a notch 76 in it. On the rear of the door 56.1 there is a protrusion 78.

A reel R of dental floss is inserted into the enclosure 26 whilst the door is held in its raised position. The floss is unreeled and drawn down into the slot 70 so that is has a free end outside the enclosure. The door is then closed and the floss pressed up into the notch 70, taken upwardly across the depressed area 74 and hooked over the cutter 72.

The protrusion 78, by engaging with the top edges of the wall portions 68, forms a latch to hold the door closed. The protrusion 78 spans between the side walls 34.1. It thus resists any tendency of the door 56.1 to move sideways when dental floss is being withdrawn and cut.

Reverting now to FIG. 1, it will be noted that the support 32 is dimensioned so that it grips the flexible part of the toothpaste tube T below the more rigid top structure TS onto which the cap C is screwed. The distance between the arms of the support 32 is less than the diameter of the tube T and hence the tube T is always squeezed somewhat by the arms of the support 32 so that the toothpaste tube T does not drop through.

The support 28 has a slightly wider portion 28.1 adjacent the plate 12 and a slightly narrower portion 28.2 outwardly of the portion 28.1. The cup 30 has, in the base thereof, a slot for receiving the support 28. The base of the cup 30 includes two claws 80 which curve towards one another, but do not meet, and which bound the slot. The width of the slot is slightly more than that of the portion 28.2, so that, as the cup is slid onto the support 28, the portion 28.2 slides through the slot until the cup encounters the opposed shoulders which exist where the portion 28.1 merges with the portion 28.2. This limits further movement of the cup towards the plate 12.

The cup 30 can be slid off the support 28, inverted, and slid back on in an upright position. The ring 82 is a separate item which is slid onto the cup over the base and caused to snap into a groove which is moulded into the cup. The ring 82 is purely decorative.

I claim:

1. A tooth brush head enclosure comprising walling defining a space for receiving a tooth brush head from which a handle protrudes, the walling comprising a bottom wall having a front edge and two spaced side walls having front edges which bound a front entrance to said space, a recess in said front edge of said bottom wall for allowing passage therethrough of the handle of the tooth brush so that the head of the tooth brush can reside in said space, and so that the handle can hang down below said enclosure, a cradle comprising protrusions extending upwardly from said bottom wall for supporting the tooth brush head which is within said space in such manner that the bristles of the tooth brush head are spaced from said bottom wall, a water drainage slot which forms an extension of said recess, said bottom wall sloping down to said slot to promote draining of the enclosure, and a door for closing off said entrance, the door having a first position in which it closes said entrance and a second position in which said entrance is open to enable the tooth brush head to be placed in said space for support by the cradle or removed from said space.

2. An enclosure according to claim 1, in which said side walls of the enclosure have free vertically extending rear edges, there being mounting means for the enclosure on the external faces of said side walls adjacent said rear edges.

3. An enclosure according to claim 2 in which said mounting means comprise protruding lugs on the external faces of said side walls adjacent said rear edges.

4. The combination of an enclosure according to claim 3 and a wall mounting plate including a recess into which said enclosure is inserted with said rear edges leading, vertical bounding faces of said recess including sockets for receiving said lugs of the enclosure thereby to mount the enclosure on said plate.

5. The combination of claim 4 and further including a support bar which protrudes from said plate and a cup having in the base thereof a slot in which said bar can be inserted to support said cup, the correct way up or inverted, on said bar.

6. The combination of claim 4 and further including a toothpaste tube support protruding from said plate, said support being bifurcated so as to provide a recess into which a toothpaste tube can be pushed, the tube hanging vertically from said support.

7. The combination of an enclosure according to claim 2 and a wall mounting plate including a recess into which said enclosure is inserted with said rear edges leading, vertical bounding faces of said recess including sockets for cooperating with said mounting means on said side walls thereby to mount said enclosure on said plate.

8. The combination according to claim 7 in which said rear edges protrude above and below said mounting plate so that a top wall of the enclosure is above the plate and said bottom wall is below the plate, there being an air flow passage between said top wall and said plate and between said bottom wall and said plate.

9. A dental floss enclosure comprising walling defining a space for receiving a reel of dental floss, the walling bounding a front entrance to said space, a door in the form of a flap having its upper end pivotally mounted on said walling and having a notch in its lower edge through which dental floss can be run from the interior of aid enclosure to the exterior, a dental floss cutter on the front of said door, the cutter being at a level above said notch so that the floss runs upwardly from said notch to the cutter, a latch at the lower end of the door for holding the door closed and for resisting sideways movement of the door when dental floss is pulled against said cutter on the door to cut off a length of floss, and a depression in the outer face of said door between the notch and the cutter whereby the portion of the floss spanning from the notch to the cutter transverses the depression.

10. In combination a plate for mounting on a wall, the plate having at least one recess in the front face thereof, two opposed bounding faces of said recess having sockets therein, and an enclosure comprising walling defining a space, said walling including a bottom wall forming the base of said space, spaced side walls having front edges defining a front entrance to the space within the enclosure and rear edges defining a rear opening which leads into said space, a door in the form of a flap which is pivotally mounted at its upper end on said walling, said door having a closed position in which it hangs down to close-off said entrance and being pivotable upwardly about its pivotal mounting to permit access to be had to said space, said walling including two outwardly protruding lugs which are received in said sockets when said enclosure is inserted into said recess whereby the interengaged sockets and lugs mount the enclosure on said plate, and said bottom wall having a recess in that edge thereof which is adjacent the door when the door is in its closed position whereby a tooth brush can hang from said enclosure with its head in said space and its handle extending downwardly from said head and through said recess to the outside of said cavity.

11. The combination according to claim 10 in which said rear edges protrude both above and below said plate so that a top wall of the enclosure is above the plate and said bottom wall is below the plate, there being an air flow passage between said top wall and said plate and between said bottom wall and said plate.

* * * * *